(12) United States Patent
Shinhama et al.

(10) Patent No.: US 9,206,169 B2
(45) Date of Patent: Dec. 8, 2015

(54) METHOD FOR PRODUCING BENZO[B]THIOPHENE COMPOUND

(75) Inventors: Koichi Shinhama, Osaka (JP); Naoto Utsumi, Osaka (JP); Masahiro Sota, Osaka (JP); Shigeo Fujieda, Osaka (JP); Shin Ogasawara, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/235,635

(22) PCT Filed: Jul. 27, 2012

(86) PCT No.: PCT/JP2012/069784
§ 371 (c)(1),
(2), (4) Date: Jan. 28, 2014

(87) PCT Pub. No.: WO2013/015456
PCT Pub. Date: Jan. 31, 2013

(65) Prior Publication Data
US 2014/0187782 A1    Jul. 3, 2014

(30) Foreign Application Priority Data
Jul. 28, 2011 (JP) .................. 2011-165724

(51) Int. Cl.
*C07D 409/12* (2006.01)
*C07D 333/54* (2006.01)

(52) U.S. Cl.
CPC ............ *C07D 409/12* (2013.01); *C07D 333/54* (2013.01)

(58) Field of Classification Search
USPC ................................ 544/363, 376
See application file for complete search history.

(56) References Cited

U.S. PATENT DOCUMENTS

| 5,929,281 A | 7/1999 | Nishiyama et al. |
| 2008/0306271 A1 | 12/2008 | Neu et al. |

FOREIGN PATENT DOCUMENTS

| CN | 101341122 A | 1/2009 |
| JP | 3161360 | 4/2001 |
| JP | 3216566 | 10/2001 |
| JP | 2006-316052 | 11/2006 |
| TW | 200409771 (A) | 6/2004 |
| WO | WO 2004/026864 A1 | 4/2004 |
| WO | WO 2006/112464 A1 | 10/2006 |

OTHER PUBLICATIONS

Surrry et al.; "Biaryl Phosphane Ligands in Palladium-Catalyzed Amination", Angewadte Chemie International Edition, vol. 47, No. 34, pp. 6338-6361, (2008).

Rataboul et al.; "New Ligands for a General Palladium-Catalyzed Amination of Aryl and Heteroaryl Chlorides", Chem. Eur. J., vol. 10, No. 12, pp. 2983-2990, (2004).

Allen et al.; "An Improved Synthesis of Subsituted Benzo[B]Thiophenes Using Microwave Irradiation", Tetrahedron Letters, vol. 45, No. 52, pp. 9645-9647, (2004).

Marion et al.; "Modified (NHC)Pd(Allyl)Cl (NHC=N-Heterocyclic Carbene) Complexes for Room-Temperature Suzuki-Miyaura and Buchwald-Hartwig Reactions", J. Am. Chem. Soc., vol. 128, No. 12, pp. 4101-4111, (2006).

Frisch et al.; "Comparison of Palladium Carbene and Palladium Phosphine Cataysts for Catalytic Coupling Reactions of Aryl Halides", Journal of Molecular Catalysis, A:Chemical, vol. 214, No. 2, pp. 231-239, (2004).

Henderson et al.; "Efficient Pd-Catalyzed Amination Reactions for Heterocycle Functionalizaton", Organic Letters, vol. 12, No. 12, No. 20, pp. 4442-4445, (2010).

Surry et al.; "Dialkylbiaryl Phosphines in Pd-Catalyzed Amination: A User's Guide", Chem. Sci., vol. 2, pp. 27-50, (2011).

International Search Report from the European Patent Office for International Application No. PCT/JP2012/069784, mailing date Nov. 16, 2012.

Written Opinion of the International Searching Authority from the European Patent Office for International Application PCT/JP2012/069784, mailing date Nov. 16, 2012.

*Primary Examiner* — Kristin Vajda
(74) *Attorney, Agent, or Firm* — Finnegan, Henderson, Farabow, Garrett & Dunner, L.L.P.

(57) ABSTRACT

The present invention provides a method for producing a compound of Formula (4): wherein $R^1$ is a hydrogen atom etc. by reacting a compound of Formula (2): wherein $X^1$ is a leaving group, with a compound of Formula (3): wherein $R^1$ is as defined above, in the presence of (a) a palladium compound and a tertiary phosphine or (b) a palladium carbene complex, in an inert solvent or without a solvent. The present invention can produce the compound of Formula (4), with high purity and high yield, and by a simple operation.

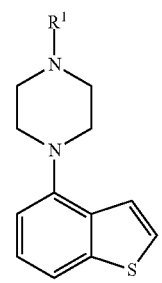

(4)

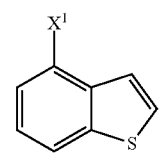

(2)

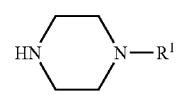

(3)

13 Claims, No Drawings

METHOD FOR PRODUCING BENZO[B]THIOPHENE COMPOUND

TECHNICAL FIELD

The present invention relates to a method for producing a benzo[b]thiophene compound.

BACKGROUND ART

A 4-(1-piperazinyl)benzo[b]thiophene compound represented by Formula (1):

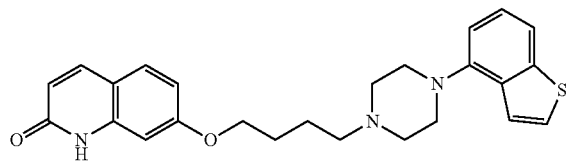

(1)

is useful for various medicines such as antipsychotic drugs. Moreover, a 4-(1-piperazinyl)benzo[b]thiophene compound represented by Formula (4):

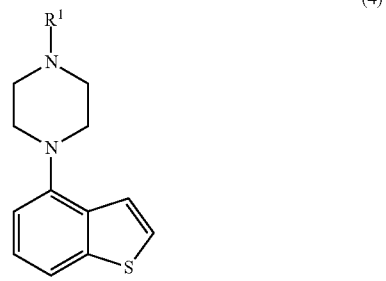

(4)

wherein $R^1$ is a hydrogen atom or a protecting group, is useful as an intermediate for synthesizing the compound represented by Formula (1).

Reference Example 30 and Example 1 of PTL 1 specifically disclose a method for producing a benzo[b]thiophene compound (the reaction scheme shown below). In Reference Example 30, 4-(1-piperazinyl)benzo[b]thiophene is produced by heating under reflux a mixture comprising 14.4 g of 4-bromobenzo[b]thiophene, 29.8 g of anhydrous piperazine, 9.3 g of sodium tert-butoxide, 0.65 g of (R)-(+)-2,2'-bis(diphenylphosphino)-1,1'-binaphthyl (BINAP), 0.63 g of tris(dibenzylideneacetone)dipalladium (0), and 250 ml of toluene (step X).

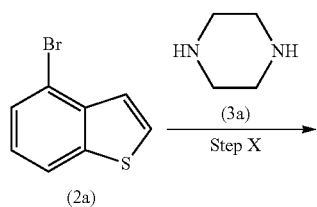

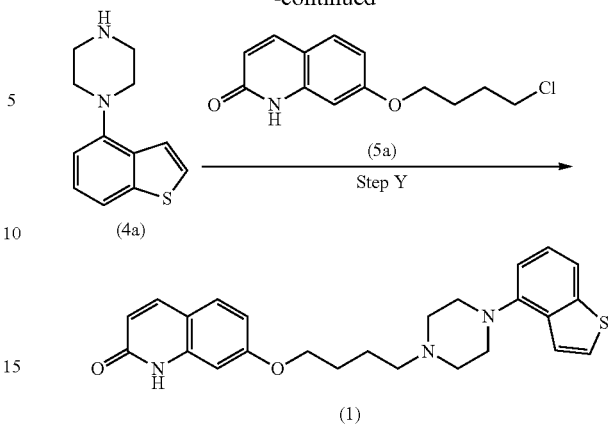

However, the reaction of the step X produces a relatively large amount of by-products that can hardly be separated, and the purity of the compound (4a) is thus inevitably reduced. Moreover, although column purification is performed to increase the purity of the compound (4a), it is very difficult to completely remove by-products, even by column chromatography purification. For this reason, there is a demand for the development of a novel method for producing the compound (4a) with high yield and high purity.

Furthermore, by-products contained in the compound (4a) inevitably reduce the purity of the compound (1) in the subsequent step Y. Since the method described in PTL 1 requires purification by column chromatography to obtain the target compound (1) with high purity, the method is not suitable for the industrial process of mass production. In addition, according to the method, incorporation of by-products that can hardly be separated is inevitable, and high-purity products usable as active pharmaceutical ingredients cannot be produced without purification by column chromatography.

CITATION LIST

Patent Literature

PTL 1: Japanese Unexamined Patent Publication No. 2006-316052 Non Patent Literature
NPL 1: Tetrahedron Lett., 2004, 45, 9645

SUMMARY OF INVENTION

Technical Problem

An object of the present invention is to provide a novel production method that can industrially advantageously produce the compound represented by Formula (1) or a salt thereof. Another object of the present invention is to provide a novel production method that can industrially advantageously produce the 4-(1-piperazinyl)benzo[b]thiophene compound represented by Formula (4), which is a precursor of the compound represented by Formula (1).

Solution to Problem

The present inventors conducted extensive research to solve the above problems, and found that the target compounds can be obtained via specific steps with high yield and high purity while suppressing the production of by-products, without performing purification by column chromatography. The present invention has been accomplished based on these findings.

The present invention provides methods according to the following Items I-1 to I-19, Items II-1 to II-21, and Items III-1 to III-39.

Item I-1. A method for producing a compound represented by Formula (4):

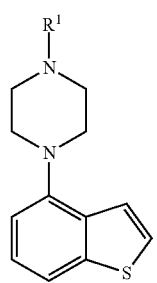

(4)

wherein $R^1$ is a hydrogen atom or a protecting group, or a salt thereof by reacting a compound represented by Formula (2):

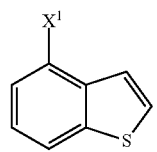

(2)

wherein $X^1$ is a leaving group, with a compound represented by Formula (3):

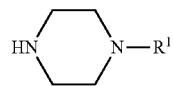

(3)

wherein $R^1$ is as defined above, or a salt thereof; the method comprising:

step A: reacting the compound represented by Formula (2) with the compound represented by Formula (3) or a salt thereof in the presence of (a) a palladium compound and a tertiary phosphine or (b) a palladium carbene complex, in an inert solvent or without a solvent.

Item I-2. The method according to Item I-1, wherein in the step A, the compound represented by Formula (2) is reacted with the compound represented by Formula (3) or a salt thereof in the presence of (a) a palladium compound and a tertiary phosphine, in an inert solvent or without a solvent.

Item I-3. The method according to Item I-1, wherein in the step A, the compound represented by Formula (2) is reacted with the compound represented by Formula (3) or a salt thereof in the presence of (b) a palladium carbene complex, in an inert solvent or without a solvent.

Item I-4. The method according to any one of Items I-1 to I-3, wherein the tertiary phosphine is at least one member selected from the group consisting of tri-tert-butylphosphine, 2-(di-tert-butylphosphino)-1,1'-biphenyl, 2-(di-tert-butylphosphino)-2'-methyl-1,1'-biphenyl, 2-(di-tert-butylphosphino)-1,1'-binaphthyl, 2-dicyclohexylphosphino-2',6'-dimethoxy-1,1'-biphenyl, 2-dicyclohexylphosphino-2',6'-di-iso-propoxy-1,1'-biphenyl, N-phenyl-2-(di-tert-butylphosphino) pyrrole, and 1-phenyl-2-(di-tert-butylphosphino)-1H-indene.

Item I-5. The method according to any one of Items I-1 to I-4, wherein the palladium carbene complex is at least one member selected from the group consisting of (1,4-naphthoquinone)-[1,3-bis(2,6-diisopropylphenyl)imidazol-2-ylidene]palladium (0), allylchloro-[1,3-bis(2,6-diisopropylphenyl)imidazol-2-ylidene]palladium (II), allylchloro-[1,3-bis(2,6-diisopropylphenyl)-4,5-dihydroimidazol-2-ylidene]palladium (II), and (3-phenylallylchloro)-[1,3-bis(2,6-diisopropylphenyl)-4,5-dihydroimidazol-2-ylidene]palladium (II).

Item I-6. The method according to any one of Items I-1 to I-5, wherein the tertiary phosphine is tri-tert-butylphosphine and/or 2-dicyclohexylphosphino-2',6'-di-iso-propoxy-1,1'-biphenyl.

Item I-7. The method according to any one of Items I-1 to I-6, wherein the palladium compound is at least one member selected from the group consisting of sodium hexachloropalladate(IV)tetrahydrate, potassium hexachloropalladate(IV), palladium(II) chloride, palladium(II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraamminepalladium(II), dichloro(cycloocta-1,5-diene)palladium(II), palladium(II)trifluoroacetate, tris(dibenzylideneacetone)dipalladium (0), tris(dibenzylideneacetone) dipalladium (0) chloroform complex, and tetrakis (triphenylphosphine)palladium (0).

Item I-8. The method according to any one of Items I-1 to I-7, wherein the palladium compound is palladium(II)acetate.

Item I-9. The method according to any one of Items I-1 to I-8, wherein the palladium carbene complex is allylchloro-[1,3-bis(2,6-diisopropylphenyl)-4,5-dihydroimidazol-2-ylidene] palladium (II).

Item I-10. The method according to any one of Items I-1 to I-9, wherein in the step A, the inert solvent is xylene and/or toluene.

Item I-11. The method according to any one of Items I-1 to I-10, wherein the leaving group represented by $X^1$ in Formula (2) is a halogen atom.

Item I-12. The method according to Item I-11, wherein the leaving group represented by $X^1$ in Formula (2) is a chlorine atom.

Item I-13. The method according to any one of Items I-1 to I-12, wherein the palladium compound is used in an amount of 0.01 to 5 mole %, in terms of palladium atom, per mole of the compound represented by Formula (2), and the tertiary phosphine is used in an amount of 0.01 to 1,000 moles per mole of palladium atom in the palladium compound.

Item I-14. The method according to Item I-13, wherein the palladium compound is used in an amount of 0.05 to 0.5 mole %, in terms of palladium atom, per mole of the compound represented by Formula (2).

Item I-15. The method according to Item I-13 or I-14, wherein the tertiary phosphine is used in an amount of 0.1 to 10 moles per mole of palladium atom in the palladium compound.

Item I-16. The method according to any one of Items I-13 to I-15, wherein the tertiary phosphine is used in an amount of 1 to 5 moles per mole of palladium atom in the palladium compound.

Item I-17. The method according to any one of Items I-1 to I-16, wherein the palladium carbene complex is used in an amount of 0.001 to 5 mole %, in terms of palladium atom, per mole of the compound represented by Formula (2).

Item I-18. The method according to Item I-17, wherein the palladium carbene complex is used in an amount of 0.01 to 0.5 mole %, in terms of palladium atom, per mole of the compound represented by Formula (2).

Item I-19. The method according to any one of Items I-1 to I-18, further comprising the step of obtaining the compound represented by Formula (2) by decarboxylation of a compound represented by Formula (6):

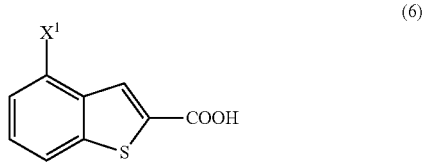

(6)

wherein $X^1$ is as defined above, or a salt thereof in the presence of a high-boiling basic compound, in a high-boiling solvent or without a solvent.

Item II-1. A method for producing a compound represented by Formula (1):

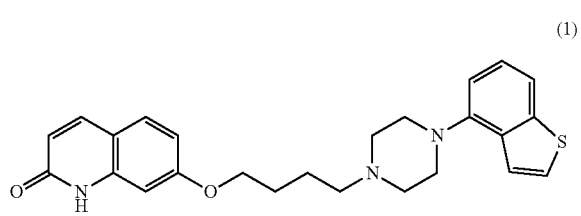 [SMILES: O=c1ccc2ccc(OCCCCN3CCN(c4cccc5sccc45)CC3)cc2[nH]1]

(1)

or a salt thereof by reacting a compound represented by Formula (4a):

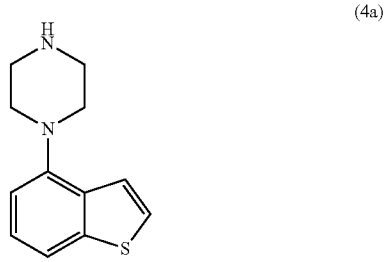 [SMILES: c1cc(N2CCNCC2)c2ccsc2c1]

(4a)

or a salt thereof with a compound represented by Formula (5):

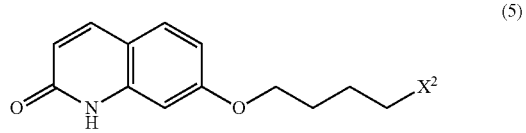

(5)

wherein $X^2$ is a leaving group, or a salt thereof; the method comprising:

step B: reacting the compound represented by Formula (4a) or a salt thereof with the compound represented by Formula (5) or a salt thereof in the presence of a basic compound, in an inert solvent or without a solvent;

step C: mixing an acetic acid and an alcohol with the reaction product obtained in the step B; and step D: adding a hydrochloric acid to the mixture obtained in the step C to obtain a hydrochloride of the compound represented by Formula (1).

Item II-2. The method according to Item II-1, further comprising:

step E: reacting the hydrochloride of the compound represented by Formula (1) obtained in the step D in the presence of a basic compound to obtain the compound represented by Formula (1).

Item II-3. The method according to Item II-2, wherein in the step E, the basic compound is sodium hydroxide.

Item II-4. The method according to Item II-2 or II-3, further comprising:

step F: converting the compound represented by Formula (1) obtained in the step E into a salt form.

Item II-5. The method according to any one of Items II-1 to II-4, wherein in the step C, the alcohol is at least one member selected from the group consisting of methanol, ethanol, and isopropyl alcohol.

Item II-6. The method according to Item II-5, wherein in the step C, the alcohol is ethanol.

Item II-7. The method according to any one of Items II-1 to II-6, wherein in the step B, the basic compound is used in an amount of 0.3 to 5 moles per mole of the compound represented by Formula (5).

Item II-8. The method according to any one of Items II-1 to II-7, wherein in the step B, the reaction is carried out further in the presence of an alkali metal halide.

Item II-9. The method according to Item II-8, wherein in the step B, the alkali metal halide is potassium iodide.

Item II-10. The method according to Item II-8 or II-9, wherein in the step B, the alkali metal halide is used in an amount of 0.1 to 10 moles per mole of the compound represented by Formula (5).

Item II-11. The method according to any one of Items II-1 to II-10, wherein in the step C, the acetic acid is used in an amount of 0.1 ml or more per gram of the compound represented by Formula (1) obtained in the step B.

Item II-12. The method according to any one of Items II-1 to II-11, wherein in the step C, the acetic acid is used in an amount of 1 ml or more per gram of the compound represented by Formula (1) obtained in the step B.

Item II-13. The method according to any one of Items II-1 to II-12, wherein in the step C, the acetic acid is used in an amount of 1.5 ml or more per gram of the compound represented by Formula (1) obtained in the step B.

Item II-14. The method according to any one of Items II-1 to II-13, wherein in the step C, the acetic acid is used in an amount of 10 ml or less per gram of the compound represented by Formula (1) obtained in the step B.

Item II-15. The method according to any one of Items II-1 to II-14, wherein in the step C, the alcohol is used in an amount of 1 to 100 ml per gram of the compound represented by Formula (1) obtained in the step B.

Item II-16. The method according to any one of Items II-1 to II-15, wherein in the step D, the hydrochloric acid is used in an amount of 1 mole or more of the molar amount of hydrogen chloride in the hydrochloric acid, per mole of the compound represented by Formula (1) obtained in the step B.

Item II-17. The method according to any one of Items II-1 to II-16, wherein in the step D, the hydrochloric acid is used in an amount of 10 moles or less of the molar amount of hydrogen chloride in the hydrochloric acid, per mole of the compound represented by Formula (1) obtained in the step B.

Item II-18. The method according to Items II-17, wherein in the step D, the hydrochloric acid is used in an amount of 2 moles or less of the molar amount of hydrogen chloride in the hydrochloric acid, per mole of the compound represented by Formula (1) obtained in the step B.

Item II-19. The method according to any one of Items II-1 to II-18, wherein in the step D, the hydrochloride is obtained by adding a hydrochloric acid at 50° C. to a reflux temperature, and cooling the mixture to 20° C. or less.

Item II-20. The method according to Item II-19, wherein in the step D, the hydrochloride is obtained by cooling the mixture to 10° C. or less.

Item II-21. The method according to any one of Items II-1 to II-20, wherein the hydrochloric acid is a concentrated hydrochloric acid.

Item III-1. A method for producing a compound represented by Formula (1):

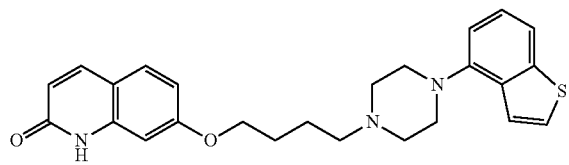

(1)

or a salt thereof by reacting a compound represented by Formula (2):

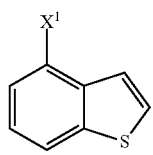

(2)

wherein $X^1$ is a leaving group, with a compound represented by Formula (3a):

(3a)

or a salt thereof, and reacting the resulting compound represented by Formula (4a):

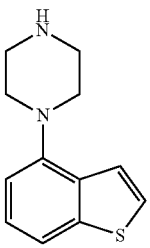

(4a)

or a salt thereof with a compound represented by Formula (5):

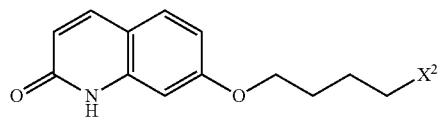

(5)

wherein $X^2$ is a leaving group, or a salt thereof; the method comprising:

step A: reacting the compound represented by Formula (2) with the compound represented by Formula (3a) or a salt thereof in the presence of (a) a palladium compound and a tertiary phosphine or (b) a palladium carbene complex, in an inert solvent or without a solvent;

step B: reacting the compound represented by Formula (4a) or a salt thereof with the compound represented by Formula (5) or a salt thereof in the presence of a basic compound, in an inert solvent or without a solvent;

step C: mixing an acetic acid and an alcohol with the reaction product obtained in the step B; and step D: adding a hydrochloric acid to the mixture obtained in the step C to obtain a hydrochloride of the compound represented by Formula (1).

Item III-2. The method according to Item III-1, wherein in the step A, the compound represented by Formula (2) is reacted with the compound represented by Formula (3) or a salt thereof in the presence of (a) a palladium compound and a tertiary phosphine, in an inert solvent or without a solvent.

Item III-3. The method according to Item III-1, wherein in the step A, the compound represented by Formula (2) is reacted with the compound represented by Formula (3) or a salt thereof in the presence of (b) a palladium carbene complex, in an inert solvent or without a solvent.

Item III-4. The method according to any one of Items III-1 to III-3, wherein in the step A, the tertiary phosphine is at least one member selected from the group consisting of tri-tert-butylphosphine, 2-(di-tert-butylphosphino)-1,1'-biphenyl, 2-(di-tert-butylphosphino)-2'-methyl-1,1'-biphenyl, 2-(di-tert-butylphosphino)-1,1'-binaphthyl, 2-dicyclohexylphosphino-2',6'-dimethoxy-1,1'-biphenyl, 2-dicyclohexylphosphino-2',6'-di-iso-propoxy-1,1'-biphenyl, N-phenyl-2-(di-tert-butylphosphino)pyrrole, and 1-phenyl-2-(di-tert-butylphosphino)-1H-indene.

Item III-5. The method according to any one of Items III-1 to III-4, wherein in the step A, the palladium carbene complex is at least one member selected from the group consisting of (1,4-naphthoquinone)-[1,3-bis(2,6-diisopropylphenyl)imidazol-2-ylidene]palladium (0), allylchloro-[1,3-bis(2,6-diisopropylphenyl)imidazol-2-ylidene]palladium (II), allylchloro-[1,3-bis(2,6-diisopropylphenyl)-4,5-dihydroimidazol-2-ylidene]palladium (II), and (3-phenylallylchloro)-[1,3-bis(2,6-diisopropylphenyl)-4,5-dihydroimidazol-2-ylidene]palladium (II).

Item III-6. The method according to any one of Items III-1 to III-5, wherein in the step A, the tertiary phosphine is tri-tert-butylphosphine and/or 2-dicyclohexylphosphino-2',6'-di-iso-propoxy-1,1'-biphenyl.

Item III-7. The method according to any one of Items III-1 to III-6, wherein in the step A, the palladium compound is at least one member selected from the group consisting of sodium hexachloropalladate(IV)tetrahydrate, potassium hexachloropalladate(IV), palladium(II) chloride, palladium (II) bromide, palladium(II)acetate, palladium(II) acetylacetonate, dichlorobis(benzonitrile)palladium(II), dichlorobis (acetonitrile)palladium(II), dichlorobis(triphenylphosphine) palladium(II), dichlorotetraamminepalladium(II), dichloro (cycloocta-1,5-diene)palladium(II), palladium(II) trifluoroacetate, tris(dibenzylideneacetone)dipalladium (0), tris(dibenzylideneacetone)dipalladium (0) chloroform complex, and tetrakis(triphenylphosphine)palladium (0).

Item III-8. The method according to any one of Items III-1 to III-7, wherein the palladium compound is palladium(II) acetate.

Item III-9. The method according to any one of Items III-1 to III-8, wherein in the step A, the palladium carbene complex is allylchloro-[1,3-bis(2,6-diisopropylphenyl)-4,5-dihydroimidazol-2-ylidene]palladium (II).

Item III-10. The method according to any one of Items III-1 to III-9, wherein in the step A, the inert solvent is xylene and/or toluene.

Item III-11. The method according to any one of Items III-1 to III-10, wherein the leaving group represented by $X^1$ in Formula (2) is a halogen atom.

Item III-12. The method according to Item III-11, wherein the leaving group represented by $X^1$ in Formula (2) is a chlorine atom.

Item III-13. The method according to any one of Items III-1 to III-12, wherein in the step A, the palladium compound is used in an amount of 0.01 to 5 mole %, in terms of palladium atom, per mole of the compound represented by Formula (2), and the tertiary phosphine is used in an amount of 0.01 to 1,000 moles per mole of palladium atom in the palladium compound.

Item III-14. The method according to Item III-13, wherein in the step A, the palladium compound is used in an amount of 0.01 to 0.5 mole %, in terms of palladium atom, per mole of the compound represented by Formula (2).

Item III-15. The method according to Item III-13 or III-14, wherein in the step A, the tertiary phosphine is used in an amount of 0.1 to 10 moles per mole of palladium atom in the palladium compound.

Item III-16. The method according to any one of Items III-13 to III-15, wherein in the step A, the tertiary phosphine is used in an amount of 1 to 5 moles per mole of palladium atom in the palladium compound.

Item III-17. The method according to any one of Items III-1 to III-16, wherein in the step A, the palladium carbene complex is used in an amount of 0.001 to 5 mole %, in terms of palladium atom, per mole of the compound represented by Formula (2).

Item III-18. The method according to Item III-17, wherein the palladium carbene complex is used in an amount of 0.01 to 0.5 mole %, in terms of palladium atom, per mole of the compound represented by Formula (2).

Item III-19. The method according to any one of Items III-1 to III-18, further comprising:

step E: reacting the hydrochloride of the compound represented by Formula (1) obtained in the step D in the presence of a basic compound to obtain the compound represented by Formula (1).

Item III-20. The method according to Item III-19, wherein in the step E, the basic compound is sodium hydroxide.

Item III-21. The method according to Item III-19 or III-20, further comprising:

step F: converting the compound represented by Formula (1) obtained in the step E into a salt form.

Item III-22. The method according to any one of Items III-1 to III-21, wherein in the step C, the alcohol is at least one member selected from the group consisting of methanol, ethanol, and isopropyl alcohol.

Item III-23. The method according to Item III-22, wherein the alcohol is ethanol.

Item III-24. The method according to any one of Items III-1 to III-23, wherein in the step B, the basic compound is used in an amount of 0.3 to 5 moles per mole of the compound represented by Formula (5).

Item III-25. The method according to any one of Items III-1 to III-24, wherein in the step B, the reaction is carried out further in the presence of an alkali metal halide.

Item III-26. The method according to Item III-25, wherein in the step B, the alkali metal halide is potassium iodide.

Item III-27. The method according to Item III-25 or III-26, wherein in the step B, the alkali metal halide is used in an amount of 0.1 to 10 moles per mole of the compound represented by Formula (5).

Item III-28. The method according to any one of Items III-1 to III-27, wherein in the step C, the acetic acid is used in an amount of 0.1 ml or more per gram of the compound represented by Formula (1) obtained in the step B.

Item III-29. The method according to any one of Items III-1 to III-28, wherein in the step C, the acetic acid is used in an amount of 1 ml or more per gram of the compound represented by Formula (1) obtained in the step B.

Item III-30. The method according to any one of Items III-1 to III-29, wherein in the step C, the acetic acid is used in an amount of 1.5 ml or more per gram of the compound represented by Formula (1) obtained in the step B.

Item III-31. The method according to any one of Items III-1 to III-30, wherein in the step C, the acetic acid is used in an amount of 10 ml or less per gram of the compound represented by Formula (1) obtained in the step B.

Item III-32. The method according to any one of Items III-1 to III-31, wherein in the step C, the alcohol is used in an amount of 1 to 100 ml per gram of the compound represented by Formula (1) obtained in the step B.

Item III-33. The method according to any one of Items III-1 to III-32, wherein in the step D, the hydrochloric acid is used in an amount of 1 mole or more of the molar amount of hydrogen chloride in the hydrochloric acid, per mole of the compound represented by Formula (1) obtained in the step B.

Item III-34. The method according to any one of Items III-1 to III-33, wherein in the step D, the hydrochloric acid is used in an amount of 10 moles or less of the molar amount of hydrogen chloride in the hydrochloric acid, per mole of the compound represented by Formula (1) obtained in the step. B.

Item III-35. The method according to Item III-34, wherein in the step D, the hydrochloric acid is used in an amount of 2 moles or less of the molar amount of hydrogen chloride in the hydrochloric acid, per mole of the compound represented by Formula (1) obtained in the step B.

Item III-36. The method according to any one of Items III-1 to III-35, wherein in the step D, the hydrochloride is obtained by adding a hydrochloric acid at 50° C. to a reflux temperature, and cooling the mixture to 20° C. or less.

Item III-37. The method according to Item III-36, wherein in the step D, the hydrochloride is obtained by cooling the mixture to 10° C. or less.

Item III-38. The method according to any one of Items III-1 to III-37, wherein the hydrochloric acid is a concentrated hydrochloric acid.

Item III-39. The method according to any one of Items III-1 to III-38, further comprising the step of obtaining the compound represented by Formula (2) by decarboxylation of a compound represented by Formula (6):

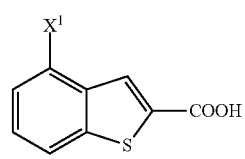

wherein $X^1$ is as defined above, or a salt thereof in the presence of a high-boiling basic compound, in a high-boiling solvent or without a solvent.

Advantageous Effects of Invention

The production method of the present invention can produce, with high purity and high yield, and by a simple operation, a compound represented by Formula (1) or a salt thereof, which is useful for various medicines such as antipsychotic drugs. Additionally, the production method of the present invention can produce, with high purity and high yield, and by a simple operation, a compound represented by Formula (4a) or a salt thereof, which is a precursor of the compound represented by Formula (1) or a salt thereof and is useful for various medicines (e.g., antipsychotic drugs) and pesticides. That is, according to the production method of the present invention, the compound represented by Formula (1) or a salt thereof, and the compound represented by Formula (4a) or a salt thereof can be produced with high purity and high yield by a simple operation, in place of column chromatography, which is an industrially disadvantageous process.

Therefore, the production method of the present invention is suitable for industrial applications.

DESCRIPTION OF EMBODIMENTS

In the present invention, a compound represented by Formula (1):

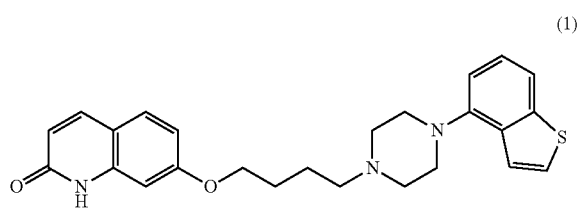 [SMILES: O=c1ccc2ccc(OCCCCN3CCN(c4cccc5sccc45)CC3)cc2[nH]1]

(1)

or a salt thereof can be produced from a benzo[b]thiophene compound represented by Formula (2):

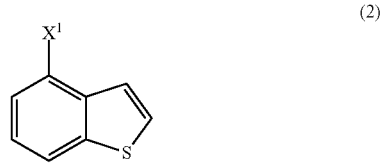

(2)

wherein $X^1$ is a leaving group, or a salt thereof via the specific steps shown below.

Reaction Scheme 1

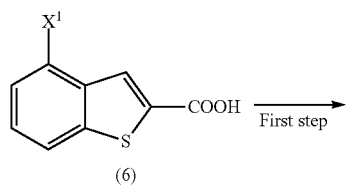

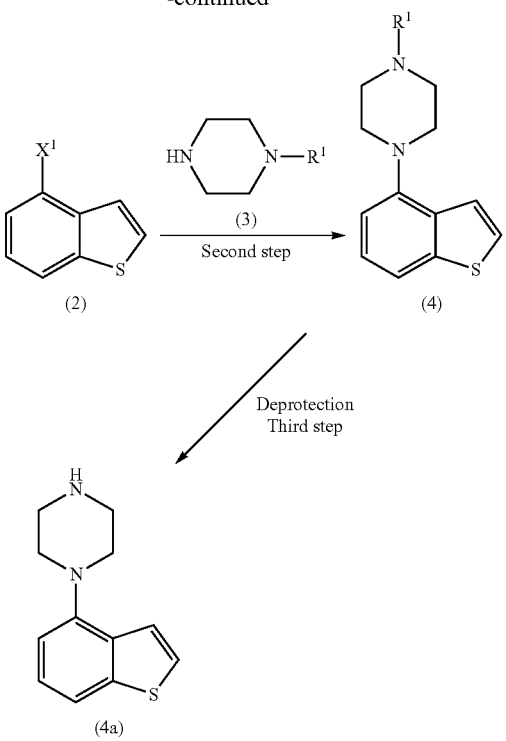

wherein $R^1$ is a hydrogen atom or a protecting group, and $X^1$ is as defined above.

The benzo[b]thiophene compound represented by Formula (2) is produced by, as shown in the above Reaction Scheme 1, decarboxylation of a compound represented by Formula (6) or a salt thereof in the presence of a high-boiling basic compound (first step).

Moreover, the 4-(1-piperazinyl)benzo[b]thiophene compound represented by Formula (4a) or a salt thereof is produced by reacting the benzo[b]thiophene compound represented by Formula (2) with a piperazine compound represented by Formula (3) or a salt thereof (second step), and optionally removing the N-protecting group of the obtained compound (third step). In the present invention, the second step is also referred to as step A.

In Formulae (6) and (2), examples of the leaving group represented by $X^1$ include halogen, lower alkylsulfonyloxy, perfluoro lower alkylsulfonyloxy, arylsulfonyloxy, aralkylsulfonyloxy, etc.

Examples of the halogen atom represented by $X^1$ include fluorine, chlorine, bromine, and iodine.

In the present invention, "lower alkyl", "lower alkoxy" and "lower alkanoyl" include "$C_{1-6}$ linear or branched alkyl", "$C_{1-6}$ linear or branched alkoxy" and "$C_{1-6}$ linear or branched alkanoyl", respectively.

Specific examples of the lower alkylsulfonyloxy group represented by $X^1$ include $C_{1-6}$ linear or branched alkylsulfonyloxy groups such as methylsulfonyloxy, ethylsulfonyloxy, n-propylsulfonyloxy, isopropylsulfonyloxy, n-butylsulfonyloxy, tert-butylsulfonyloxy, n-pentylsulfonyloxy, and n-hexylsulfonyloxy.

Specific examples of the perfluoro lower alkylsulfonyloxy group represented by $X^1$ include $C_{1-6}$ linear or branched perfluoroalkylsulfonyloxy groups such as trifluoromethylsulfonyloxy, 1,1,2,2,2-pentafluoro-1-ethylsulfonyloxy, 1,1,2,2,3,3,3-hepta-1-propylsulfonyloxy, and 1,1,2,2,3,3,4,4,4-nonafluoro-1-butylsulfonyloxy.

Examples of the arylsulfonyloxy group represented by X' include phenylsulfonyloxy groups optionally having, on the phenyl ring, 1 to 3 substituents selected from the group consisting of $C_{1-6}$ linear or branched alkyl groups, $C_{1-6}$ linear or branched alkoxy groups, nitro groups, and halogen atoms; and naphthylsulfonyloxy groups. Specific examples of the phenylsulfonyloxy group optionally having a substituent include phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy, 3-chlorophenylsulfonyloxy, and the like. Specific examples of naphthylsulfonyloxy groups include α-naphthylsulfonyloxy, β-naphthylsulfonyloxy, and the like.

Examples of the aralkylsulfonyloxy group represented by $X^1$ include $C_{1-6}$ linear or branched alkylsulfonyloxy groups substituted with a phenyl group optionally having, on the phenyl ring, 1 to 3 substituents selected from the group consisting of $C_{1-6}$ linear or branched alkyl groups, $C_{1-6}$ linear or branched alkoxy groups, nitro groups, and halogen atoms; and $C_{1-6}$ linear or branched alkylsulfonyloxy groups substituted with a naphthyl group. Specific examples of alkylsulfonyloxy groups substituted with a phenyl group include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, and the like. Specific examples of alkylsulfonyloxy groups substituted with a naphthyl group include α-naphthylmethylsulfonyloxy, β-naphthylmethylsulfonyloxy, and the like.

First Step:

The compound represented by Formula (6) or a salt thereof is subjected to decarboxylation without a solvent or in a high-boiling solvent, in the presence of a high-boiling basic compound, thereby producing a compound represented by Formula (2).

Examples of high-boiling solvents include ethers such as diethylene glycol dimethyl ether and dibutyl ether; aromatic hydrocarbons such as toluene, xylene, and mesitylene; alcohols such as 1-hexanol, 2-hexanol, 3-hexanol, 1-heptanol, 2-heptanol, 3-heptanol, 1-octanol, 2-octanol, 3-octanol, 1-nonaol, 2-nonaol, 1-decanol, 2-decanol, and 4-decanol; ketones such as 2-octanone, 3-octanone, 2-nonanone, 3-nonanone, 5-nonanone, 2-decanone, 3-decanone, and 4-decanone; polar solvents such as N,N-dimethylformamide (DMF), dimethylsulfoxide (DMSO), N,N-dimethylacetamide (DMA), 1,3-dimethyl-2-imidazolidinone (DMI), hexamethylphosphoric triamide, and tris(dimethylamino)phosphine. Among these high-boiling solvents, solvents having a boiling point of 160° C. or more are preferable, and DMI is particularly preferable.

As the high-boiling basic compound, known basic compounds having a melting point of 200° C. or more can be widely used. Examples thereof include organic bases such as 1,8-diazabicyclo[5.4.0]undec-7-ene (DBU) and 1,5-diazabicyclo[4.3.0]non-5-ene (DBN). These high-boiling basic compounds can be used singly or in combination of two or more. Among these high-boiling basic compounds, DBU is preferable.

The amount of high-boiling basic compound used is generally about 0.05 to 10 moles, and preferably about 0.1 to 6 moles, per mole of the compound of Formula (6).

The reaction of the first step can be carried out under reduced, normal, or elevated pressure, and can also be carried out in an inert gas atmosphere such as nitrogen or argon.

The above reaction is generally performed at ambient temperature to 300° C., preferably 150 to 250° C., and is generally completed in about 1 to 30 hours.

According to the first step, the decarboxylation reaction proceeds well without using a reaction solvent, and the amount of high-boiling basic compound (e.g., DBU) used is lower. Thus, the first step has not only economic advantages but also benefits of simplifying treatment after reaction.

Second Step (Step A):

The compound represented by Formula (2) is reacted with a compound represented by Formula (3) without a solvent or in an inert solvent, in the presence or absence of a basic compound and in the presence of (a) a catalyst comprising a tertiary phosphine and a palladium compound or (b) a palladium carbene complex, thereby producing a compound represented by Formula (4).

The compound represented by Formula (3) is a known compound, or can be easily produced from a known compound.

Examples of inert solvents include water; ethers such as dioxane, tetrahydrofuran, diethyl ether, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as DMF, DMSO, hexamethylphosphoric triamide, and acetonitrile.

As the palladium compound used in the reaction, known palladium compounds can be widely used. Examples thereof include tetravalent palladium compounds such as sodium hexachloropalladate(IV)tetrahydrate and potassium hexachloropalladate(IV); divalent palladium compounds such as palladium(II) chloride, palladium(II) bromide, palladium(II)acetate, palladium(II) acetylacetonate, dichlorobis(benzonitrile)palladium(II), dichlorobis(acetonitrile)palladium(II), dichlorobis(triphenylphosphine)palladium(II), dichlorotetraamminepalladium(II), dichloro(cycloocta-1,5-diene)palladium(II), and palladium(II)trifluoroacetate; zerovalent palladium compounds such as tris(dibenzylideneacetone)dipalladium (0), tris(dibenzylideneacetone)dipalladium (0) chloroform complex, and tetrakis(triphenylphosphine)palladium (0); and the like. These palladium compounds can be used singly or in combination of two or more.

The amount of palladium compound used is not particularly limited, and can be suitably selected from a wide range. For example, the palladium compound can be generally used in an amount of 0.000001 to 20 mole %, in terms of palladium atom, per mole of the compound represented by Formula (2). When the amount of palladium compound is within this range, the compound of Formula (4) can be produced with high selectivity. From the viewpoint of producing the target compound with high yield in a short time and from an economic viewpoint, it is preferable to use the palladium compound in an amount of about 0.0001 to 20 mole %, more preferably about 0.0001 to 5 mole %, even more preferably about 0.01 to 5 mole %, and particularly preferably about 0.01 to 0.5 mole %, in terms of palladium atom, per mole of the compound represented by Formula (2).

As the tertiary phosphine used in combination with the palladium compound in the present invention, known tertiary phosphines can be widely used. Specific examples thereof include trialkylphosphines such as triethylphosphine, tri-cyclohexylphosphine, tri-isopropylphosphine, tri-n-butylphosphine, tri-iso-butylphosphine, tri-sec-butylphosphine, and tri-tert-butylphosphine; triarylphosphines such as triphenylphosphine, tri-pentafluorophenylphosphine, tri-o-tolylphosphine, tri-m-tolylphosphine, and tri-p-tolylphosphine; phenoxyphosphines such as tri(2,6-dimethylphenoxy)phosphine, tri(2-tert-butylphenoxy)phosphine, triphenoxy phosphine, tri(4-methylphenoxy)phosphine, and tri(2-methylphenoxy)phosphine; and biarylphosphines such as 2,2'-bis(diphenylphosphino)-1,1'-binaphthyl (racemic body), (R)-(+)-2,2'-bis(diphenylphosphino)-1,1'-binaphthyl, and (S)-(+)-2,2'-bis(diphenylphosphino)-1,1'-binaphthyl, 2-(di-tert-butylphosphino)-1,1'-biphenyl (JohnPhos), 2-dicyclohexylphosphino-2'-methylbiphenyl (MePhos), 2-dicyclohexylphosphino-2',6'-dimethoxy-1,1'-biphenyl (SPhos), 2-(dicyclohexylphosphino)-2'-(N,N-dimethylamino)biphenyl (DavePhos), and 2-(dicyclohexylphosphino)-2',6'-di-iso-propoxy-1,1'-biphenyl (RuPhos). These tertiary phosphines can be used singly or in combination of two or more. More preferred tertiary phosphines are trialkylphosphines such as tri-tert-butylphosphine, and biarylphosphines such as 2-(dicyclohexylphosphino)-2',6'-di-iso-propoxy-1,1'-biphenyl (RuPhos).

In terms of suppressing the progress of side reactions, preferable tertiary phosphines to be used in the present invention are tri-tert-butylphosphine and biarylphosphines such as 2-(di-tert-butylphosphino)-1,1'-biphenyl (hereinafter "L1"), 2-(di-tert-butylphosphino)-2'-methyl-1,1'-biphenyl (hereinafter "L2"), 2-(di-tert-butylphosphino)-1,1'-binaphthyl (hereinafter "L5"), 2-dicyclohexylphosphino-2',6'-dimethoxy-1,1'-biphenyl (hereinafter "L10"), 2-dicyclohexylphosphino-2',6'-di-iso-propoxy-1,1'-biphenyl (RuPhos) (hereinafter "L12"), N-phenyl-2-(di-tert-butylphosphino)pyrrole (hereinafter "L16"), and 1-phenyl-2-(di-tert-butylphosphino)-1H-indene (hereinafter "L17"). More preferable among these are tri-tert-butylphosphine and L12.

Furthermore, the tertiary phosphine used in the present invention may be prepared in a salt form in advance. Specific examples of such salts include tri-tert-butylphosphonium tetraphenylborate and tri-tert-butylphosphonium tetrafluoroborate.

The amount of tertiary phosphine used is generally about 0.01 to 10,000 moles per mole of palladium atom in the palladium compound. It is preferable to use the tertiary phosphine in an amount of about 0.1 to 1,000 moles, more preferably about 0.1 to 10 moles, and particularly preferably about 1 to 5 moles, per mole of palladium atom in the palladium compound.

Suitable combinations of a palladium compound and a tertiary phosphine include combinations of a palladium compound selected from the group consisting of palladium acetate, bis(dibenzylideneacetone)palladium, tris(dibenzylideneacetone)dipalladium, tetrakis(triphenylphosphine)palladium, palladium chloride, dichlorobis(triphenylphosphine)palladium, and dichlorobis(tri-o-tolylphosphine)palladium; and a tertiary phosphine selected from the group consisting of 2-(di-tert-butylphosphino)-1,1'-biphenyl, 2,8,9-triisobutyl-2,5,8,9-tetraaza-1-phosphabicyclo[3,3,3]undecane, N-phenyl-2-(di-tert-butylphosphino)indole, N-phenyl-2-(di-tert-butylphosphino)pyrrole, tri-tert-butylphosphine, 4,5-bis(diphenylphosphino)-9,9-dimethylxanthene, tri-tert-butylphosphonium tetraphenylborate, and tri-tert-butylphosphonium tetrafluoroborate. Particularly preferable combinations are the combination of palladium acetate and tri-tert-butylphosphonium tetraphenylborate, and the combination of palladium acetate and RuPhos.

In terms of suppressing the progress of side reactions, preferable combinations of a palladium compound and a tertiary phosphine are combinations of palladium acetate and tri-tert-butylphosphine, L1, L2, L5, L10, L12, L16, or L17, and more preferable combinations are combinations of palladium acetate and tri-tert-butylphosphine or L12.

The palladium compound and the tertiary phosphine may be prepared in a complex form in advance. When the palladium compound and the tertiary phosphine are used in a complex form, the above-mentioned combinations of a palladium compound and a tertiary phosphine can be used. The amount of complex is preferably the same as the above-mentioned amount of palladium compound.

As the palladium carbene complex, known palladium carbene complexes can be widely used. Specific examples thereof include (1,4-naphthoquinone)-[1,3-bis(2,6-diisopropylphenyl)imidazol-2-ylidene]palladium (0) (hereinafter "CX11"), (1,4-naphthoquinone)-[1,3-bis(2,4,6-trimethylphenyl)imidazol-2-ylidene]palladium (0) (hereinafter "CX12"), allylchloro-[1,3-bis(2,6-diisopropylphenyl)imidazol-2-ylidene]palladium (II) (hereinafter "CX21"), allylchloro-[1,3-bis(2,4,6-trimethylphenyl)imidazol-2-ylidene]palladium (II) (hereinafter "CX22"), allylchloro-[1,3-bis(2,6-diisopropylphenyl)-4,5-dihydroimidazol-2-ylidene]palladium (II) (hereinafter "CX23"), (3-phenylallylchloro)-[1,3-bis(2,4,6-trimethylphenyl)-imidazol-2-ylidene]palladium (II) (hereinafter "CX31"), (3-phenylallylchloro)-[1,3-bis(2,6-diisopropylphenyl)-4,5-dihydroimidazol-2-ylidene]palladium (II) (hereinafter "CX32"), dichloro-[1,3-bis(2,6-diisopropylphenyl)imidazol-2-ylidene]palladium (II)dimer (hereinafter "CX41"), and other palladium complexes of N-heterocyclic carbene. These palladium carbene complexes can be used singly or in combination of two or more. In terms of suppressing the progress of side reactions, preferable palladium carbene complexes to be used in the present invention are CX11, CX21, CX23, CX32, and other palladium complexes of N-heterocyclic carbene. More preferable are CX11, CX21, CX23, and CX32.

The amount of palladium carbene complex used is not particularly limited, and can be suitably selected from a wide range. For example, the palladium carbene complex can be generally used in an amount of about 0.0001 to 20 mole %, in terms of palladium atom, per mole of the compound represented by Formula (2). When the amount of palladium carbene complex is within this range, the compound of Formula (4) can be produced with high selectivity. From the viewpoint of producing the target compound with high yield in a short time and from an economic viewpoint, it is preferable to use the palladium carbene complex in an amount of about 0.001 to 5 mole %, and more preferably about 0.01 to 0.5 mole %, in terms of palladium atom, per mole of the compound represented by Formula (2).

The palladium carbene complex may be prepared in a complex form in advance, or may be formed in a reaction system from a palladium compound as mentioned above and a corresponding carbene precursor. Usable carbene precursors are corresponding N-heterocyclic halide salts. Specific examples thereof include 1,3-bis(2,6-diisopropylphenyl)imidazolium chloride, 1,3-bis(2,4,6-trimethylphenyl)imidazolium chloride, 1,3-bis(2,6-diisopropylphenyl)-4,5-dihydroimidazolium chloride, 1,3-bis(2,4,6-trimethylphenyl)-4,5-dihydroimidazolium chloride, and other 1,3-disubstituted imidazolium salts or 1,3-disubstituted dihydroimidazolium salts. The amount of palladium compound used in this case may be the same as the amount of the aforementioned palladium carbene complex in terms of palladium atom. Moreover, the amount of carbene precursor used is generally in the range of about 0.0001 to 20 mole % per mole of the compound represented by Formula (2). From the viewpoint of producing the target compound with high yield in a short time and from an economic viewpoint, it is preferable to use the carbene precursor in an amount of about 0.001 to 5 mole %, and more preferably about 0.01 to 0.5 mole %, per mole of the compound represented by Formula (2).

As the basic compound, known basic compounds can be widely used. Examples thereof include alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; inorganic bases such as sodium amide, sodium hydride, and potassium hydride; alkali metal alkoxides such as sodium methoxide, sodium ethoxide, potassium methoxide, potassium ethoxide, lithium tert-butoxide, sodium tert-butoxide, and potassium tert-butoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, DBN, DBU, and 1,4-diazabicyclo[2.2.2]octane (DABCO). These basic compounds can be used singly or in combination of two or more. A preferred basic compound is alkali metal alkoxide.

The basic compound is generally used in an amount of about 0.5 to 10 moles, and preferably about 0.5 to 6 moles, per mole of the compound of Formula (2).

The compound of Formula (3) is generally used in an amount of at least about 0.5 moles, and preferably about 0.5 to 5 moles, per mole of the compound of Formula (2).

The reaction of the second step can be carried out under normal or elevated pressure, and can also be carried out in an inert gas atmosphere such as nitrogen or argon.

The above reaction is generally performed at ambient temperature to 200° C., preferably at ambient temperature to 150° C., and is generally completed in about 1 to 30 hours.

Third Step:

In the compound represented by Formula (4) or a salt thereof obtained in the second step, when $R^1$ is an N-protecting group, the compound or a salt thereof is subjected to removal of the N-protecting group, thereby producing the compound (4a) or a salt thereof.

Preferable examples of the "N-protecting group" include mono-, di-, or triphenyl(lower)alkyl (e.g., benzyl, phenethyl, 1-phenylethyl, benzhydryl, and trityl), lower alkanoyl (e.g., formyl, acetyl, propionyl, hexanoyl, and pivaloyl), mono- (or di- or tri-)halo(lower)alkanoyl (e.g., chloroacetyl and trifluoroacetyl), lower alkoxycarbonyl (e.g., methoxycarbonyl, ethoxycarbonyl, and tert-butoxycarbonyl), mono- (or di- or tri-)halo(lower)alkoxycarbonyl (e.g., chloromethoxycarbonyl, dichloroethoxycarbonyl, and trichloroethoxycarbonyl), aroyl (e.g., benzoyl, toluoyl, xyloyl, and naphthoyl), phenyl (lower)alkanoyl (e.g., phenylacetyl and phenylpropionyl), phenyl(lower)alkoxycarbonyl optionally having nitro or lower alkoxy (e.g., benzyloxycarbonyl, phenethyloxycarbonyl, p-nitrobenzyloxycarbonyl, and p-methoxybenzyloxycarbonyl), lower alkylsulfonyl (e.g., methylsulfonyl, ethylsulfonyl, propylsulfonyl, isopropylsulfonyl, pentylsulfonyl, and butylsulfonyl), arylsulfonyl (e.g., phenylsulfonyl, tolylsulfonyl, xylylsulfonyl, and naphthylsulfonyl), and phenyl (lower)alkylsulfonyl (e.g., benzylsulfonyl, phenethylsulfonyl, and benzhydrylsulfonyl).

More preferable examples of the "N-protecting group" include triphenyl $(C_{1-4})$alkyl, $(C_{1-4})$alkanoyl, and $(C_{1-4})$alkoxycarbonyl, and particularly preferably tert-butoxycarbonyl.

The removal of the N-protecting group (deprotection) is performed by a known method such as hydrolysis or reduction.

Hydrolysis:

Hydrolysis is preferably carried out in the presence of base or acid, including a Lewis acid.

Examples of suitable bases include inorganic bases such as alkali metal hydroxides (e.g., sodium hydroxide and potassium hydroxide), alkali earth metal hydroxides (e.g., magnesium hydroxide and calcium hydroxide), alkali metal carbonates (e.g., sodium carbonate and potassium carbonate), alkaline earth metal carbonates (e.g., magnesium carbonate and calcium carbonate), and alkali metal hydrogencarbonates (e.g., sodium hydrogencarbonate and potassium hydrogencarbonate); and organic bases such as trialkylamine (e.g., trimethylamine and triethylamine), picoline, DBN, DBU, and DABCO.

Suitable acids are organic acids (e.g., formic acid, acetic acid, propionic acid, trichloroacetic acid, and trifluoroacetic acid) and inorganic acids (e.g., hydrochloric acid, hydrobromic acid, and sulfuric acid).

Deprotection using a Lewis acid such as trihaloacetic acid (e.g., trichloroacetic acid or trifluoroacetic acid), is preferably carried out in the presence of a cation scavenger (e.g., anisole or phenol).

Hydrolysis is performed in a commonly used solvent that does not adversely affect the reaction. Examples thereof include water; alcohols such as methanol, ethanol, trifluoroethanol, and ethylene glycol; acetone; ethers such as diethyl ether, dioxane, and tetrahydrofuran; halogenated hydrocarbons such as chloroform, methylene chloride, and ethylene chloride; esters such as methyl acetate and ethyl acetate; acetonitrile and DMF; and mixtures thereof. When the base or acid is liquid, the base or acid can also be used as a solvent.

The hydrolysis reaction is generally carried out while cooling or heating, or at ambient temperature.

Reduction:

Known reduction reaction such as chemical reduction and catalytic reduction can be applied to reduction.

Preferable reducing agents used in chemical reduction are, for example, combinations of hydrides (e.g., lithium aluminum hydride, sodium borohydride, sodium cyanoborohydride, and diisopropyl aluminum hydride), metals (e.g., tin, zinc, and iron), or metal compounds (e.g., chromium chloride and chromium acetate) with organic or inorganic acids (e.g., formic acid, acetic acid, propionic acid, trifluoroacetic acid, p-toluenesulfonic acid, hydrochloric acid, and hydrobromic acid).

Preferable catalysts used in catalytic reduction are platinum catalysts (e.g., platinum plates, platinum sponge, platinum black, colloidal platinum, platinum oxide, and platinum wires), palladium catalysts (e.g., palladium sponge, palladium black, palladium oxide, palladium-carbon, colloidal palladium, palladium-barium sulfate, and palladium-barium carbonate), nickel catalysts (e.g., reduced nickel, nickel oxide, and Raney nickel), cobalt catalysts (e.g., reduced cobalt and Raney cobalt), iron catalysts (e.g., reduced iron and Raney iron), and copper catalysts (e.g., reduced copper, Raney copper, and Ullmann copper).

The reduction reaction is performed in a commonly used solvent that does not adversely affect the reaction. Examples thereof include water; alcohols such as methanol, ethanol, trifluoroethanol, and ethylene glycol; acetone; ethers such as diethyl ether, dioxane, and tetrahydrofuran; halogenated hydrocarbons such as chloroform, methylene chloride, and ethylene chloride; esters such as methyl acetate and ethyl acetate; acetonitrile, DMF, and pyridine; and mixtures thereof.

The reduction reaction is generally carried out while cooling or heating, or at ambient temperature, preferably at ambient temperature to 100° C., for about 0.5 to 10 hours.

Furthermore, the aforementioned deprotection of the N-protecting group is not limited to the above reaction conditions. For example, the reaction described in T. W. Green and P. G. M. Wuts, "Protective Groups in Organic Synthesis" 2nd ed., John Wiley & Sons; New York, 1991, p. 309, can be applied to the third step.

Reaction Scheme 2

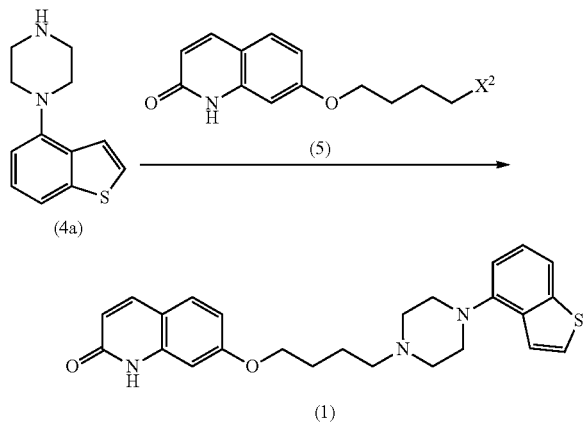

wherein $X^2$ is a leaving group.

In Formula (5), examples of the leaving group represented by $X^2$ include those mentioned as examples of the leaving group represented by $X^1$ such as halogen, lower alkylsulfonyloxy, perfluoro lower alkylsulfonyloxy, arylsulfonyloxy, and aralkylsulfonyloxy.

The compound represented by Formula (5) is a known compound, and can be produced by a known method.

Step B:

As shown in the above Reaction Scheme 2, the compound represented by Formula (1) or a salt thereof can be produced by reacting a 4-(1-piperazinyl)benzo[b]thiophene compound represented by Formula (4a) or a salt thereof with a compound represented by Formula (5) or a salt thereof without a solvent or in an inert solvent, in the presence of a basic compound. In the step B, an alkali metal halide is preferably present in the reaction system.

The compound of Formula (4a) or a salt thereof is used in an amount of about 0.5 to 5 moles, preferably about 0.9 to 2 moles, and more preferably about 1 to 1.2 moles, per mole of the compound of Formula (5) or salt thereof.

As the basic compound, known basic compounds can be widely used. Examples thereof include alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; inorganic bases such as sodium amide, sodium hydride, and potassium hydride; alkali metal alkoxides such as sodium methoxide, sodium ethoxide, potassium methoxide, potassium ethoxide, lithium tert-butoxide, sodium tert-butoxide, and potassium tert-butoxide; organic bases such as triethylamine, tripropylamine, pyridine, quinoline, piperidine, imidazole, N-ethyldiisopropylamine, dimethylaminopyridine, trimethylamine, dimethylaniline, N-methylmorpholine, DBN, DBU, and DABCO. These basic compounds can be used singly or in combination of two or more. Preferable basic compounds include alkali metal carbonates.

The basic compound is generally used in an amount of about 0.3 to 5 moles, and preferably about 1 to 2 moles, per mole of the compound of Formula (5).

Examples of alkali metal halides include potassium iodide and sodium iodide. These alkali metal halides can be used singly or in combination of two or more. Preferable alkali metal halides include potassium iodide.

The alkali metal halide is generally used in an amount of about 0.1 to 10 moles, and preferably about 1 to 1.2 moles, per mole of the compound of Formula (5).

Examples of inert solvents include water; ethers such as dioxane, tetrahydrofuran, diethyl ether, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as DMF, DMSO, hexamethylphosphoric triamide, and acetonitrile.

The above reaction is generally performed at ambient temperature to 200° C., preferably at ambient temperature to 150° C., and is generally completed in about 1 to 30 hours.

In the Reaction Scheme 2, the compound represented by Formula (1) or a salt thereof can be produced with high purity by a simple method including the following steps C and D. That is, the compound represented by Formula (1) or a salt thereof, which is sufficiently applicable to medicine applications, can be obtained with high purity via the steps C and D, without performing purification by column chromatography.

Step C:

A solution of the compound represented by Formula (1) can be obtained by mixing an acetic acid and an alcohol with the compound represented by Formula (1), which is a reaction product obtained in the step B.

Examples of alcohols include methanol, ethanol, isopropyl alcohol, n-propyl alcohol, tert-butyl alcohol, and the like. Preferable are methanol, ethanol, and isopropyl alcohol, and more preferable is ethanol. These alcohol solvents can be used singly or in combination of two or more.

In the step C, the acetic acid and alcohol can be mixed simultaneously or separately. More specifically, a mixed solvent of the acetic acid and alcohol can be mixed with the compound of Formula (1); or one of the acetic acid and alcohol is first mixed with the compound of Formula (1), and the other is then mixed.

The amount of acetic acid used may be 0.1 ml or more, preferably 1 ml or more, and more preferably 1.5 ml or more, per gram of the compound represented by Formula (1) obtained in the step B. Although the upper limit of the amount is not particularly limited, the amount of acetic acid used is, for example, 10 ml or lower per gram of the compound represented by Formula (1) obtained in the step B.

The alcohol solvent may be used in an amount that allows sufficient dissolution of the compound represented by Formula (1) and precipitation of the hydrochloride represented by Formula (1) in the step D described later. For example, the above purification method can be performed using 1 to 100 ml of alcohol solvent per gram of the compound represented by Formula (1) obtained in the step B.

In the step C, solvents other than acetic acid and alcohol may be mixed. Examples of such a solvent include water and other solvents.

Step D:

A hydrochloride of the compound represented by Formula (1) can be obtained by adding a hydrochloric acid to the mixture obtained in the step C.

Examples of hydrochloric acids include concentrated hydrochloric acids and hydrochloric acids with a normality of 1 to 12. A mixed solution of an alcohol (e.g., methanol, ethanol, or isopropyl alcohol) and a concentrated hydrochloric acid or hydrochloric acids with a normality of 1 to 12 can also be used. In addition, a solution prepared by dissolving hydrogen chloride in an organic solvent such as an alcohol (e.g., methanol, ethanol, or isopropyl alcohol), ether (e.g., dioxane), or ester (e.g., ethyl acetate), can also be used.

As the amount of hydrochloric acid used, the molar amount of hydrogen chloride in the hydrochloric acid is preferably 1 mole or more per mole of the compound represented by Formula (1) obtained in the step B. Although the upper limit of the amount is not particularly limited, the molar amount of hydrogen chloride in the hydrochloric acid is, for example, 10 moles or lower, and preferably 2 moles or lower per mole of the compound represented by Formula (1) obtained in the step B.

The temperature at which the step D is performed is not particularly limited; for example, the hydrochloride can be obtained by adding a hydrochloric acid at around 50° C. to a reflux temperature, and cooling the mixture to 20° C. (preferably 10° C.) or less.

By employing a production method including the above steps B, C, and D, hardly removable by-products can be removed by a simple method, without using a purification method such as column chromatography, and the compound represented by Formula (1) or a salt thereof can be produced with high yield and high purity.

Step E:

The compound represented by Formula (1) can also be obtained by further reacting the hydrochloride of the compound of Formula (1) obtained in the step D in a mixture of water and alcohol (e.g. methanol, ethanol, isopropylalcohol) in the presence of a basic compound.

The mixture of water and alcohol used in step E can be obtained by, for example, mixing alcohol with water in an amount such that the volume ratio of water to alcohol is 0.1 to 10.

As the basic compound, known basic compounds can be widely used. Examples thereof include alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; inorganic bases such as sodium amide, sodium hydride, and potassium hydride; alkali metal alkoxides such as sodium methoxide, sodium ethoxide, potassium methoxide, potassium ethoxide, lithium tert-butoxide, sodium tert-butoxide, and potassium tert-butoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, DBN, DBU, and DABCO. These basic compounds can be used singly or in combination of two or more. A preferred basic compound is alkali metal alkoxide. Preferred basic compounds are alkali metal hydroxides such as sodium hydroxide, potassium hydroxide, cesium hydroxide, and lithium hydroxide; and alkaline earth metal hydroxides such as calcium hydroxide. A more preferred basic compound is sodium hydroxide.

The temperature at which the step E is performed is not particularly limited; for example, the compound of Formula (1) can be obtained by adding the basic compound at around 60° C. to a reflux temperature, and cooling the mixture to 50° C. (preferably 40° C.) or less.

Step F:

A salt of the compound represented by Formula (1) can be obtained by further converting the compound of Formula (1) obtained in the step E into a salt form. As the method for obtaining the salt of the compound of Formula (1), known methods generally used can be used. For example, a compound corresponding to the target salt (e.g., acid such as hydrochloric acid) is reacted in a solution of the compound represented by Formula (1).

In the method shown in the above Reaction Scheme 1, the compound (6) used as a starting material may be an easily available known compound, or can be easily produced by a known method. For example, the compound (6) can be produced by a method shown in the following Reaction Scheme 3:

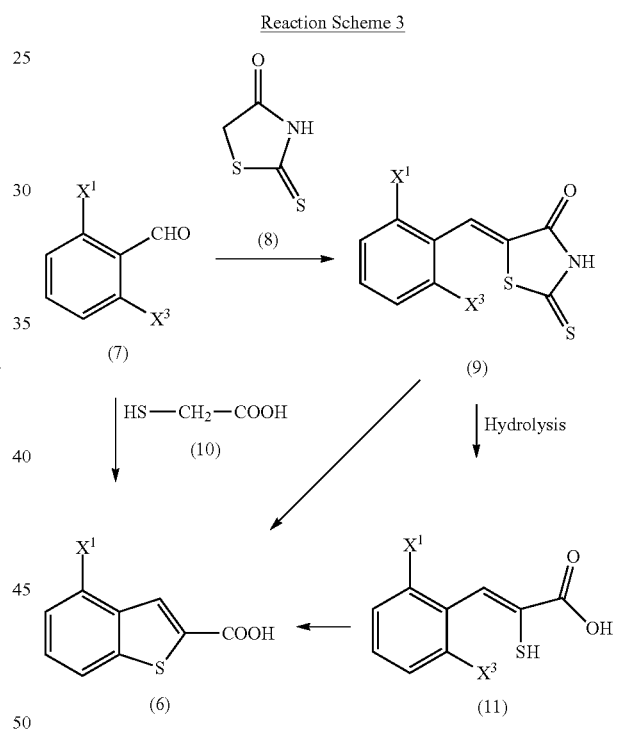

Reaction Scheme 3 wherein $X^1$ is as defined above, and $X^3$ is halogen (fluorine, chlorine, bromine, or iodine).

The compounds represented by Formulae (7) to (11) are known compounds, or can be easily produced from known compounds.

These series of reactions can be performed by the methods disclosed in Reference Examples 1 to 8, or by methods similar to those methods.

The starting compound used in each of the above reaction schemes may be a preferable salt. Moreover, the target compound obtained in each reaction may form a preferable salt. Examples of such preferable salts include preferable salts of the compounds (1) and (4a) exemplified below.

Preferable salts of the compounds (1) and (4a) are pharmacologically acceptable salts. Examples thereof include metal salts such as alkali metal salts (e.g., sodium salts and potassium salts) and alkaline earth metal salts (e.g., calcium salts and magnesium salts); ammonium salts; salts of other inorganic bases such as alkali metal carbonates (e.g., lithium carbonate, potassium carbonate, sodium carbonate, and cesium carbonate), alkali metal hydrogencarbonates (e.g., lithium hydrogencarbonate, sodium hydrogencarbonate, and potassium hydrogencarbonate), and alkali metal hydroxides (e.g., lithium hydroxide, sodium hydroxide, potassium hydroxide, and cesium hydroxide); salts of organic bases such as tri(lower)alkylamines (e.g., trimethylamine, triethylamine, and N-ethyldiisopropylamine), pyridine, quinoline, piperidine, imidazole, picoline, dimethylaminopyridine, dimethylaniline, N-(lower)alkylmorpholine (e.g., N-methylmorpholine), DBN, DBU, and DABCO; inorganic acid salts such as hydrochloride, hydrobromate, hydriodate, sulfate, nitrate, and phosphate; organic acid salts such as formate, acetate, propionate, oxalate, malonate, succinate, fumarate, maleate, lactate, malate, citrate, tartrate, citrate, carbonate, picrate, methanesulfonate, ethanesulfonate, p-toluenesulfonate, and glutamate; and the like.

Each of the target compounds obtained according to the above reaction schemes can be isolated and purified from the reaction mixture by, for example, cooling the reaction mixture, followed by an isolation procedure such as filtration, concentration, or extraction, to separate a crude reaction product, and then subjecting the crude reaction product to a usual purification procedure, such as recrystallization. From the industrial viewpoint, the purification procedure is preferably recrystallization or the like.

The compounds of Formulae (1) and (4a) according to the present invention naturally include geometrical isomers, stereoisomers, optical isomers, and like isomers.

EXAMPLES

The present invention is described below in more detail with reference to Reference Examples and Examples.

Reference Example 1

Synthesis of 2,6-dichlorobenzylidenerhodanine 2,6-Dichlorobenzaldehyde (77.0 g), rhodanine (58.6 g), and acetic acid (539 ml) were suspended with stirring at room temperature. Anhydrous sodium acetate (116 g) was added to the suspension, and the resulting mixture was heated under reflux for 3 hours. The reaction mixture was cooled to 45° C., and ice water (700 ml) was added. After the mixture was stirred for 0.2 hours, the precipitated crystals were collected by filtration, washed with water, and then dried to obtain 2,6-dichlorobenzylidenerhodanine. Even in non-dried form, this product could be subjected to the subsequent step.

Yield: 125.4 g
$^1$H-NMR (CDCl$_3$) δ ppm;
7.30-7.44 (3H, m), 7.70 (1H, s), 9.6 (1H, br.)

Reference Example 2

Synthesis of 2-chloro-6-fluorobenzylidenerhodanine

2-Chloro-6-fluorobenzaldehyde (9.50 g), rhodanine (7.98 g), and acetic acid (57 ml) were stirred at room temperature. Anhydrous sodium acetate (14.0 g) was added to the obtained suspension, and the mixture was heated with stirring for 2 hours. The reaction mixture was allowed to cool to room temperature, and ice water (190 ml) was added thereto. The precipitated crystals were collected by filtration, washed with water, and then dried to obtain 2-chloro-6-fluorobenzylidenerhodanine.

Yield: 15.7 g
$^1$H-NMR(CDCl$_3$) δ ppm;
7.37-7.64 (4H, m), 13.9 (1H, br.).

Reference Example 3

Synthesis of (Z)-3-(2,6-dichlorophenyl)-2-mercapto-2-propenoic acid

A suspension of 2,6-dichlorobenzylidenerhodanine (160.4 g) and water (800 ml) was stirred at room temperature, and sodium hydroxide (83.0 g) was added over a period of 1 hour. The resulting mixture was heated with stirring for another 0.5 hours. The reaction mixture was cooled with ice (10° C.), and concentrated hydrochloric acid (192 ml) was added. After the mixture was stirred while cooling with ice for 0.5 hours, the precipitated crystals were collected by filtration. The crystals obtained by filtration were washed with water and then dried to obtain an equivalent amount of (Z)-3-(2,6-dichlorophenyl)-2-mercapto-2-propenoic acid.

Yield: 138.9 g
$^1$H-NMR (DMSO-d$_6$) δ ppm;
7.23-7.67 (4H, m), 3.5-5.7 (1H, br.), 11.7-14.5 (1H, br.).

Reference Example 4

Synthesis of 2-carboxy-4-chlorobenzo[b]thiophene

A suspension of (Z)-3-(2,6-dichlorophenyl-2-mercapto-2-propenoic acid (72.4 g) and water (362 ml) was stirred at room temperature. Further, potassium hydroxide (40.8 g) was added, and the mixture was heated under reflux for 4 hours. After the mixture was allowed to cool, the mixture was stirred for 1 hour while cooling with ice. The precipitated crystals ((Z)-3-(2,6-dichlorophenyl-2-mercapto-2-propenoic acid potassium salt) were collected by filtration and washed with cold water. After the crystals were suspended in water, 35% concentrated hydrochloric acid (32 ml) was added (pH=1), and the mixture was stirred at room temperature for 1 hour. The precipitated crystals were collected by filtration and dried to obtain 2-carboxy-4-chlorobenzo[b]thiophene.

Yield of 48.8 g
$^1$H-NMR (DMSO-d$_6$) δ ppm;
7.53 (1H, t, J=7.7 Hz), 7.58 (1H, dd, J=7.7, 1.3 Hz), 8.03 (1H, d, J=0.5 Hz), 8.07 (1H, d, J=7.6 Hz).

Reference Example 5

Synthesis of sodium 4-chlorobenzo[b]thiophen-2-carboxylate

After sodium hydroxide (4.55 g) was dissolved in water (50 ml), 2,6-dichlorobenzylidenerhodanine (10.00 g) was added. The mixture was stirred under reflux for 5 hours, and then cooled to room temperature. The precipitated crystals were collected by filtration and washed with cold water to obtain sodium 4-chlorobenzo[b]thiophen-2-carboxylate.

Yield: 7.24 g
$^1$H-NMR (DMSO-d$_6$) δ ppm;
7.39 (t, J=7.7 Hz, 1H), 7.47 (dd, J=7.7, 1.0 Hz, 1H), 7.73 (d, J=0.8 Hz, 1H), 7.93 (dt, J=7.9, 0.9 Hz, 1H).

Reference Example 6

Synthesis of 2-carboxy-4-chlorobenzo[b]thiophene

Sodium 4-chlorobenzo[b]thiophen-2-carboxylate (2.40 g) was dissolved in water (33 ml) at 60° C. Concentrated hydrochloric acid (1.3 ml) was added to the solution at the same temperature, and the resulting mixture was stirred. The precipitated crystals were collected by filtration, washed with water, and then dried to obtain 2-carboxy-4-chlorobenzo[b]thiophene.

Yield: 1.61 g
$^1$H-NMR (DMSO-$d_6$);
7.53 (1H, t, J=7.7 Hz), 7.58 (1H, dd, J=7.7, 1.3 Hz), 8.03 (1H, d, J=0.5 Hz), 8.07 (1H, d, J=7.6 Hz).

Reference Example 7

Synthesis of 2-carboxy-4-chlorobenzo[b]thiophene

After potassium hydroxide (30.8 g) was dissolved in water (179 ml), thioglycolic acid (19.4 g) was added to the solution, and 2,6-dichlorobenzaldehyde (32.0 g) was further added. The resulting mixture was heated under reflux for 2.5 hours. The mixture was allowed to cool, and then allowed to stand at room temperature overnight. The precipitated crystals (potassium 4-chlorobenzo[b]thiophen-2-carboxylate) was collected by filtration and washed with cold water. Further, the crystals were dispersed in water (256 ml). After concentrated hydrochloric acid (20 ml) was added thereto, the resulting mixture was stirred for 1 hour. The precipitated crystals were collected by filtration and washed with water. Crude crystals of this 2-carboxy-4-chlorobenzo[b]thiophene were dispersed in ethyl acetate (96 ml), and washed at room temperature. The precipitated crystals were washed with ethyl acetate, and then dried to yield 29.12 g of a dried product. The dried product was further washed with ethyl acetate, and the wash was concentrated to 70 ml. The precipitated secondary crystals were collected and dried to obtain 2-carboxy-4-chlorobenzo[b]thiophene (1.35 g).

Yield: 30.5 g
White crystals
$^1$H-NMR (DMSO-$d_6$) δ ppm;
7.53 (1H, t, J=7.7 Hz), 7.58 (1H, dd, J=7.7, 1.3 Hz), 8.03 (1H, d, J=0.5 Hz), 8.07 (1H, d, J=7.6 Hz).

Reference Example 8

Synthesis of 4-chlorobenzo[b]thiophene

A mixture of 2-carboxy-4-chlorobenzo[b]thiophene (7.24 g), quinoline (36 ml), and copper powder (1.45 g) was stirred at 145 to 155° C. for 1 hour. After the mixture was allowed to cool to room temperature, the mixture was diluted with diisopropyl ether (145 ml), and insoluble materials were removed by filtration. The filtrate was washed with dilute hydrochloric acid (40 ml of 35% concentrated hydrochloric acid+200 ml of cold water) and with water, then dried over magnesium sulfate, and concentrated. A trace amount of precipitates was further removed from the concentrate by filtration to obtain 4-chlorobenzo[b]thiophene.

Yield: 5.59 g
Light brown oil
$^1$H-NMR (DMSO-$d_6$) δ ppm;
7.38 (1H, t, J=8.4 Hz), 7.51 (1H, dd, J=5.5, 0.8 Hz), 7.48 (1H, dd, J=7.7, 0.9 Hz), 7.94 (1H, dd, J=5.5, 0.4 Hz), 8.02 (1H, dt, J=8.0, 0.9 Hz).

Example 1

Synthesis of 4-chlorobenzo[b]thiophene

A mixture of 2-carboxy-4-chlorobenzo[b]thiophene (50.00 g), 1,3-dimethyl-2-imidazolidinone (DMI; 200 ml), and 1,8-diazabicyclo[5.4.0]-undec-7-ene (140.7 ml) was heated at 160 to 195° C. with stirring for 6 hours. After the mixture was cooled to 10° C., the mixture was added to 3N-hydrochloric acid (350 ml) cooled to 10° C. After the mixture was extracted with toluene (500 ml), the toluene layer was washed with 3N-hydrochloric acid, water, aqueous sodium bicarbonate solution, water, saline, and water in this order, and then concentrated to obtain 4-chlorobenzo[b]thiophene.

Yield: 36.78 g
$^1$H-NMR (DMSO-$d_6$) δ ppm;
7.38 (1H, t, J=8.4 Hz), 7.51 (1H, dd, J=5.5, 0.8 Hz), 7.48 (1H, dd, J=7.7, 0.9 Hz), 7.94 (1H, dd, J=5.5, 0.4 Hz), 8.02 (1H, dt, J=8.0, 0.9 Hz).

Example 2

Synthesis of 4-(1-piperazinyl)benzo[b]thiophene hydrochloride

4-Chlorobenzo[b]thiophene (5.00 g), piperazine (5.11 g), palladium acetate (II) (2.7 mg), tri-tert-butylphosphonium tetraphenylborate (6.2 mg), sodium tert-butoxide (8.548 g), and xylene (70 ml) were stirred at 120 to 130° C. for 5 hours. After the reaction mixture was cooled to room temperature, water was added thereto, and the layers were separated. The xylene layer was washed with water, and then with saline. After addition of activated carbon, the mixture was stirred at room temperature for 30 minutes. After filtration of the mixture, concentrated hydrochloric acid was added to the filtrate, and the resulting mixture was stirred at room temperature for 30 minutes. The precipitated crystals were collected by filtration and dried to obtain 4-(1-piperazinyl)benzo[b]thiophene hydrochloride.

Yield: 6.94 g
$^1$H-NMR (DMSO-$d_6$) δ ppm;
3.30 (4H, br.s), 3.61 (4H, br.s), 6.97 (1H, d, J=7.8 Hz), 7.32 (1H, br. dd, J=8.4, 7.8 Hz), 7.53 (1H, d, J=5.6 Hz), 7.70 (1H, d, J=8.4 Hz), 7.76 (1H, d, J=5.6 Hz), 9.37 (1H, br.s).

Example 3

Synthesis of 4-(1-piperazinyl)benzo[b]thiophene hydrochloride

4-Chlorobenzo[b]thiophene (10.0 g) and xylene (100 ml) were placed in a reaction vessel. The reaction vessel was evacuated and then purged with argon. Subsequently, piperazine (15.3 g), sodium tert-butoxide (17.1 g), palladium acetate (II) (13.0 mg), and 2-dicyclohexylphosphino-2',6'-di-iso-propoxy-1,1'-biphenyl (RuPhos) (69.0 mg) were added. After evacuation and purging with argon, the mixture was refluxed for 2 hours. After the reaction mixture was cooled to about 80° C., water (50 ml) and silica #600H (0.65 g) were added. The mixture was stirred at, approximately 60° C. for about 10 minutes, and then filtered. After the filtrate was separated into layers, the xylene layer was washed with water. Subsequently, the xylene layer was placed into the reaction vessel again. After addition of water (200 ml) and concentrated hydrochloric acid (8.0 ml), the mixture was heated with stirring for dissolution. The layers were separated at 75° C. or more. After the aqueous layer was collected, toluene (150 ml) and 25% aqueous sodium hydroxide solution (16 ml) were added, and the mixture was stirred. The layers were separated, and the organic layer was collected. The organic layer was washed with water and concentrated with an evaporator. Methanol (150 ml) was added to the concentrated oil to dissolve the oil, thus producing a methanol solution. 2-Propanol (150 ml) and concentrated hydrochloric acid (7 ml) were placed into another reaction vessel, and the methanol solution was added dropwise over a period of 15 minutes or more. After completion of the dropwise addition, the mixture was cooled and stirred at 10° C. or less for about 30 minutes, and then filtered (washed with a mixture of 5 ml of methanol and 5 ml of 2-propanol). The crystals were collected, and then dried to obtain 4-(1-piperazinyl)benzo[b]thiophene hydrochloride.

Yield: 11.61 g

1H-NMR (DMSO-$d_6$) δ ppm;

3.25-3.40 (8H, br.s), 6.96 (1H, d, J=7.5 Hz), 7.32 (1H, dd, J=8.0, 7.5 Hz), 7.52 (1H, d, J=5.5 Hz), 7.70 (1H, d, J=8.0 Hz), 7.75 (1H, d, J=5.5 Hz), 9.35 (1H, br.s).

Reference Example 9

Synthesis of 7-(4-chlorobutoxy)-1H-quinolin-2-one

After 7-hydroxy-1H-quinolin-2-one (10 g) and DMF (50 ml) were heated to approximately 30° C., an aqueous potassium carbonate solution (potassium carbonate: 8.6 g, water: 10 ml) was added. After the mixture was stirred at 30 to 40° C. for about 15 minutes, 1-bromo-4-chlorobutane (14.3 ml) was added and stirred at approximately 40° C. for 5 hours. Water (100 ml) was added dropwise over a period of 30 minutes or more while the temperature was maintained at 30° C. or more. After the mixture was stirred at approximately 30° C. for 30 minutes, stirring was continued at 10° C. or less for 1 hour, after which the precipitated crystals were collected by filtration. After methanol (100 ml) was added to the precipitated crystals, the mixture was stirred under reflux to ensure dissolution. This solution was cooled and stirred at 30 to 40° C. for 30 minutes and then at 5° C. or less for about 1 hour, after which the precipitated crystals were collected by filtration. The crystals were dried at 60° C. to obtain 7-(4-chlorobutoxy)-1H-quinolin-2-one as white powder.

Yield: 12.3 g $^1$H-NMR (300 MHz; CDCl$_3$) δ ppm;

1.95-2.05 (4H, m), 3.64 (2H, t, J=6.0 Hz), 4.10 (2H, t, J=5.5 Hz), 6.56 (1H, d, J=9.5 Hz), 6.80 (1H, dd, J=9.0 Hz, 2.5 Hz), 6.84 (1H, d, J=2.5 Hz), 7.45 (1H, d, J=9.0 Hz), 7.73 (1H, d, J=9.5 Hz), 12.45 (1H, brs).

Example 4

Synthesis of 7-[4-(4-benzo[b]thiophen-4-yl-piperazin-1-yl)butoxy]-1H-quinolin-2-one After 1-benzo[b]thiophen-4-yl-piperazine hydrochloride (10.6 g), potassium carbonate (5.8 g), and DMF (50 ml) were stirred at 30 to 40° C. for about 30 minutes, 7-(4-chlorobutoxy)-1H-quinolin-2-one (10.0 g) and potassium iodide (6.9 g) were added. The mixture was stirred at 90 to 100° C. for 2 hours. While the temperature of the mixture was maintained at 60° C. or more, water (150 ml) was added dropwise over a period of 10 minutes or more. After the mixture was cooled to 10° C. or less, the precipitated crystals were collected by filtration, and washed with water and then with ethanol.

After ethanol (325 ml) and acetic acid (25 ml) were added to the precipitated crystals, the mixture was stirred under reflux for dissolution. Concentrated hydrochloric acid (3.6 ml) was added at around 70° C., and the mixture was cooled. After confirming the precipitation of crystals, the mixture was heated again and stirred under reflux for 1 hour. After the mixture was cooled to 10° C. or less, the precipitated crystals were collected by filtration and washed with ethanol.

After ethanol (191 ml) and water (127 ml) were added to the precipitated crystals, the mixture was stirred under reflux for dissolution. After activated carbon (0.89 g) was added, the mixture was stirred under reflux for 30 minutes and then hot filtered. After activated carbon was removed, the mixture was heated again for dissolution. After 25% aqueous sodium hydroxide solution (5.8 ml) was added at approximately 70° C., the mixture was stirred under reflux for 30 minutes, after which water (64 ml) was added at approximately 70° C. After the mixture was stirred at 40° C. for 30 minutes, the precipitated crystals were collected by filtration at 40° C. or less, then washed with water, and dried to obtain 7-[4-(4-benzo[b]thiophen-4-yl-piperazin-1-yl)butoxy]-1H-quinolin-2-one as white crystals.

Yield: 14.30 g $^1$H-NMR (DMSO-$d_6$) δ ppm;

1.6-1.75 (2H, m), 1.75-1.9 (2H, m), 2.44 (2H, t, J=7.0 Hz), 2.55-2.70 (4H, m), 3.00-3.15 (4H, m), 4.06 (2H, t, J=6.3 Hz), 6.30 (1H, d, J=9.5 Hz), 6.75-6.85 (2H, m), 6.88 (1H, d, J=7.5 Hz), 7.27 (1H, dd, J=8 Hz, 8 Hz), 7.40 (1H, d, J=5.5 Hz), 7.55 (1H, d, J=9.5 Hz), 7.61 (1H, d, J=8 Hz), 7.69 (1H, d, J=5.5 Hz), 7.80 (1H, d, J=9.5 Hz), 11.58 (1H, bs).

Example 5

A palladium compound and a tertiary phosphine compound, or a palladium carbene complex, used in the second step (step A) was investigated.

Example 5a

4-Chlorobenzo[b]thiophene (500 mg) and xylene (5 ml) were placed in a reaction vessel. Subsequently, piperazine (766 mg) was added thereto, and the reaction vessel was purged with argon gas. Subsequently, sodium tert-butoxide (855 mg), palladium acetate (II) (6.6 mg, 1.0 mol %), and 2-(di-tert-butylphosphino)-1,1'-biphenyl (17.6 mg, 2.0 mol %) were placed in the reaction vessel. The reaction vessel was evacuated and then purged with argon. Subsequently, the reaction was allowed to proceed under reflux for 3 hours. After the reaction, a portion of the suspension was sampled, and unreacted materials and the reaction product contained in the reaction suspension were analyzed using high-performance liquid chromatography (HPLC) (column; XBridge C8 (4.6 mm I.D.×15 cm), eluate; 10 mmol/L aqueous sodium dodecyl sulfate (SDS) solution:acetonitrile:acetic acid=50: 50:1, 290 nm, flow rate: 1.0 ml/min, temperature: 30° C.). Table 1 below shows the results.

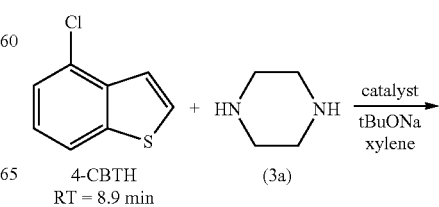

-continued

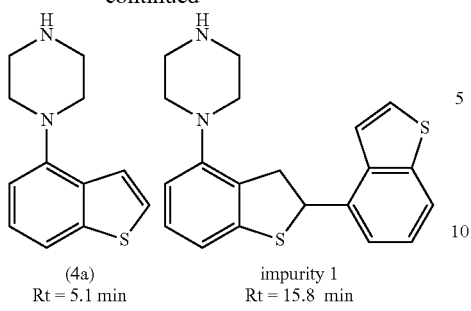

(4a)
Rt = 5.1 min impurity 1
Rt = 15.8 min

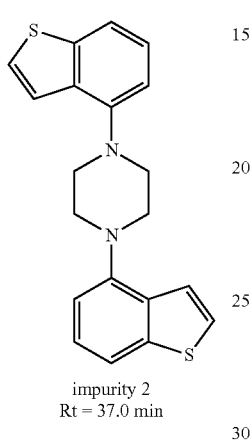

impurity 2
Rt = 37.0 min

Rt is the retention time under the above-mentioned conditions in HPLC, tBu is tert-butyl and 4-CBTH stands for 4-chlorobenzo[b]thiophene.

Examples 5b to 5g

The reaction product contained in the reaction suspension was analyzed in the same manner as in Example 5a, except that the tertiary phosphine compounds (the above L2, L5, L10, L12, L16, and L17) (2.0 mol %) were used in place of 2-(di-tert-butylphosphino)-1,1'-biphenyl (L1). Table 1 below shows the results.

L1

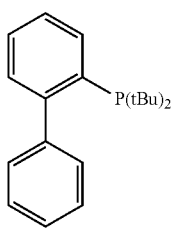

L2

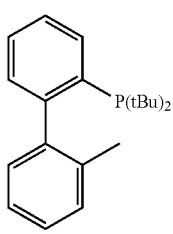

-continued

L5

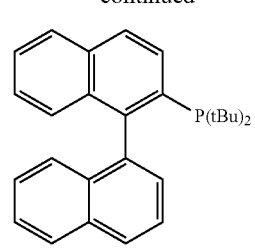

L10

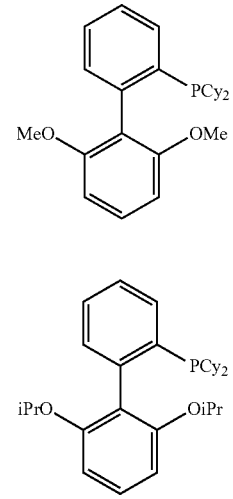

L12

L16

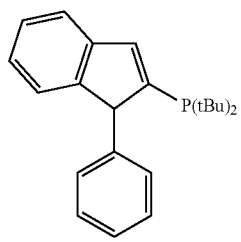

L17

In the above formulas, Me is methyl, tBu is tert-butyl, iPr is isopropyl, and Cy is cyclohexyl.

Example 6

Examples 6a to 6d

The reaction product contained in the reaction suspension was analyzed in the same manner as in Example 5a, except that palladium carbene complexes (the above CX11, CX21, CX23, and CX32) (1.0 mol %) were used in place of palladium acetate (II) and L1. Table 1 below shows the results.

CX11

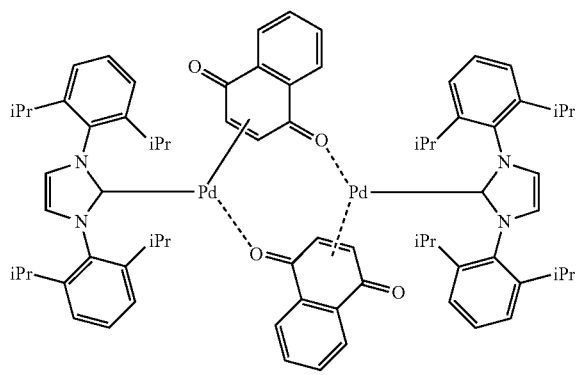

CX21

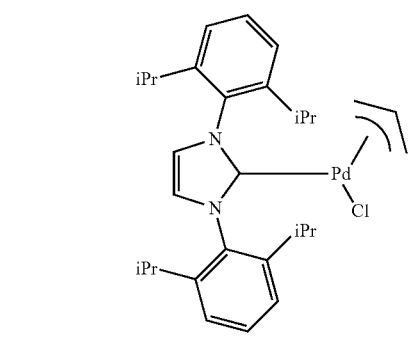

CX23

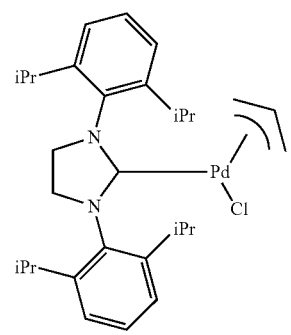

CX32

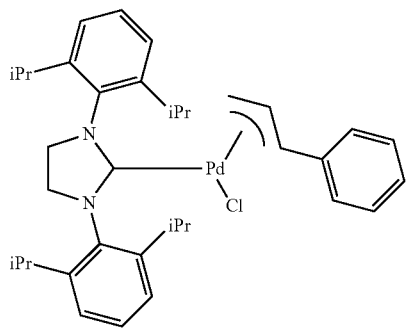

iPr is as defined above.

Example 7

The reaction product contained in the reaction suspension was analyzed in the same manner as in Example 5a, except that the amount of palladium acetate (II) used in Example 5a was changed to 0.08 mol %, and tri-tert-butylphosphonium tetraphenylborate (0.12 mol %) was used in place of 2-(di-tert-butylphosphino)-1,1'-biphenyl. Table 1 shows the results.

TABLE 1

| Example | Tertiary phosphine or carbene complex | HPLC area % | | | |
| --- | --- | --- | --- | --- | --- |
| | | (4a) | 4-CBTH | Impurity 1 | Impurity 2 |
| 5a | L1 | 68.55 | N.D. | 0.14 | 9.99 |
| 5b | L2 | 65.08 | 16.19 | 0.07 | 2.22 |
| 5c | L5 | 64.72 | 15.10 | 0.13 | 2.14 |
| 5d | L10 | 88.29 | N.D. | 0.98 | 2.04 |
| 5e | L12 | 80.03 | N.D. | 0.41 | 4.20 |
| 5f | L16 | 82.57 | 0.01 | 0.06 | 7.20 |
| 5g | L17 | 74.64 | 0.02 | 0.01 | 14.26 |
| 6a | CX11 | 83.74 | 0.03 | 0.44 | 6.58 |
| 6b | CX21 | 92.33 | 0.02 | 0.63 | 1.85 |
| 6c | CX23 | 96.08 | N.D. | 0.28 | 0.13 |
| 6d | CX32 | 87.56 | 0.02 | 0.45 | 5.51 |
| 7 | TTBuP-K | 81.42 | 0.13 | 0.30 | 1.83 |

In Table 1, each numerical yield value was calculated from the area of the peak area in HPLC. TTBuP-K is tri-tert-butylphosphonium tetraphenylborate, and 4-CBTH is as defined above.

INDUSTRIAL APPLICABILITY

The present invention provides an industrially advantageous method for producing a benzo[b]thiophene compound that is useful as an intermediate in the synthesis of various pharmaceuticals such as antipsychotic drugs, pesticides, etc. In particular, this method can be advantageously performed in the field of pharmaceutical manufacturing.

The invention claimed is:

1. A method for producing a compound represented by Formula (4):

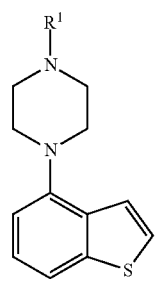

(4)

wherein $R^1$ is a hydrogen atom or a protecting group, or a salt thereof by reacting a compound represented by Formula (2):

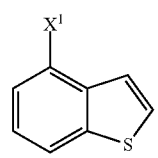

(2)

wherein $X^1$ is a leaving group, with a compound represented by Formula (3):

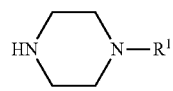

(3)

wherein R¹ is as defined above, or a salt thereof; the method comprising:
  step A: reacting the compound represented by Formula (2) with the compound represented by Formula (3) or a salt thereof in the presence of (a) a palladium compound and a tertiary phosphine or (b) a palladium carbene complex, in an inert solvent or without a solvent;
  wherein the tertiary phosphine is at least one member selected from the group consisting of tri-tert-butylphosphine, 2-(di-tert-butylphosphino)-1,1'-biphenyl, 2-(di-tert-butylphosphino)-2'-methyl-1,1'-biphenyl, 2-(di-tert-butylphosphino)-1,1'-binaphthyl, 2-dicyclohexylphosphino-2',6'-dimethoxy-1,1'-biphenyl, 2-dicyclohexylphosphino-2',6'-di-iso-propoxy-1,1'-biphenyl, N-phenyl-2-(di-tert-butylphosphino)pyrrole, and 1-phenyl-2-(di-tert-butylphosphino)-1H-indene.

2. The method according to claim 1, wherein the palladium carbene complex is at least one member selected from the group consisting of (1,4-naphthoquinone)-[1,3-bis(2,6-diisopropylphenyl)imidazol-2-ylidene]palladium(0), allylchloro-[1,3-bis(2,6-diisopropylphenyl)imidazol-2-ylidene]palladium(II), allylchloro-[1,3-bis(2,6-diisopropylphenyl)-4,5-dihydroimidazol-2-ylidene]palladium(II), and (3-phenylallylchloro)-[1,3-bis(2,6-diisopropylphenyl)-4,5-dihydroimidazol-2-ylidene]palladium(II).

3. The method according to claim 1, further comprising the step of obtaining the compound represented by Formula (2) by decarboxylation of a compound represented by Formula (6):

(6)

wherein X¹ is as defined above, or a salt thereof in the presence of a high-boiling basic compound, in a high-boiling solvent or without a solvent.

4. A method for producing a compound represented by Formula 1:
  Formula (1):

(1)

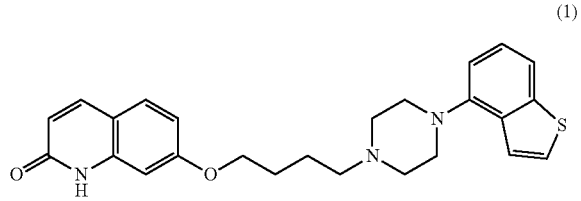 [SMILES: O=c1ccc2ccc(OCCCCN3CCN(c4cccc5sccc45)CC3)cc2[nH]1]

or a salt thereof comprising producing a compound represented by Formula (4):

Formula (4):

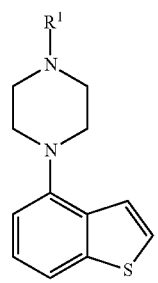

(4)

wherein R¹ is a protecting group, or a salt thereof according to the method of claim 1;
  obtaining a compound represented by Formula (4a):

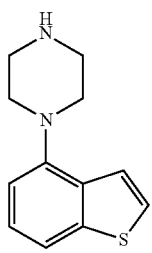

(4a)

or a salt thereof by removing the protecting group of the compound represented by Formula (4);
  step B: reacting the compound represented by Formula (4a) or a salt thereof with the compound represented by Formula (5):

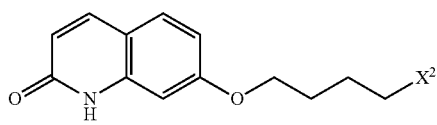

(5)

wherein X² is a leaving group, or a salt thereof in the presence of a basic compound, in an inert solvent or without a solvent.

5. A method for producing a compound represented by Formula 1:
  Formula (1):

(1)

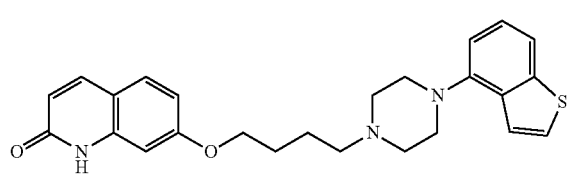

or a salt thereof comprising producing a compound represented by Formula (4):

Formula (4):

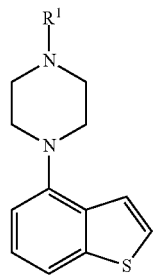

wherein R¹ is hydrogen, or a salt thereof according to the method of claim 1;

step B: reacting the compound represented by Formula (4) or a salt thereof with the compound represented by Formula (5):

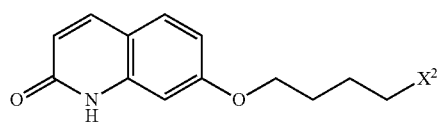

wherein $X^2$ is a leaving group, or a salt thereof in the presence of a basic compound, in an inert solvent or without a solvent.

6. The method according to claim 4, further comprising:
   step C: mixing an acetic acid and an alcohol with the reaction product obtained in the step B; and
   step D: adding a hydrochloric acid to the mixture obtained in the step C to obtain a hydrochloride of the compound represented by Formula (1).

7. The method according to claim 6, further comprising:
   step E: reacting the hydrochloride of the compound represented by Formula (1) obtained in the step D in the presence of a basic compound to obtain the compound represented by Formula (1).

8. The method according to claim 7, further comprising:
   step F: converting the compound represented by Formula (1) obtained in the step E into a salt form.

9. The method according to claim 6, wherein the alcohol is at least one member selected from the group consisting of methanol, ethanol, and isopropyl alcohol.

10. The method according to claim 5, further comprising:
    step C: mixing an acetic acid and an alcohol with the reaction product obtained in the step B; and
    step D: adding a hydrochloric acid to the mixture obtained in the step C to obtain a hydrochloride of the compound represented by Formula (1).

11. The method according to claim 10, further comprising:
    step E: reacting the hydrochloride of the compound represented by Formula (1) obtained in the step D in the presence of a basic compound to obtain the compound represented by Formula (1).

12. The method according to claim 11, further comprising:
    step F: converting the compound represented by Formula (1) obtained in the step E into a salt form.

13. The method according to claim 10, wherein the alcohol is at least one member selected from the group consisting of methanol, ethanol, and isopropyl alcohol.

* * * * *